United States Patent [19]

Sones et al.

[11] Patent Number: 4,980,904
[45] Date of Patent: Dec. 25, 1990

[54] RADIATION IMAGING CALIBRATION

[75] Inventors: Richard A. Sones, Cleveland Heights; Karen L. Lauro, South Euclid; Rodney A. Mattson, Mentor, all of Ohio

[73] Assignee: Picker International, Inc., Cleveland, Ohio

[21] Appl. No.: 219,905

[22] Filed: Jul. 13, 1988

Related U.S. Application Data

[63] Continuation of Ser. No. 798,427, Nov. 15, 1985.

[51] Int. Cl.$^5$ .............................................. G01D 18/00
[52] U.S. Cl. .................... 378/207; 250/252.1
[58] Field of Search ................ 378/5, 17–19, 378/99, 157–159, 207, 62; 250/252.1, 385; 333/81 R, 81 A; 358/111

[56] References Cited

U.S. PATENT DOCUMENTS

| | | | |
|---|---|---|---|
| 3,937,963 | 2/1976 | Hounsfield | 378/207 |
| 3,974,386 | 8/1976 | Mistretta et al. | 378/99 |
| 4,029,963 | 6/1977 | Alvarez et al. | 378/5 |
| 4,055,771 | 10/1977 | Goodenough et al. | 378/207 |
| 4,126,789 | 11/1978 | Vogl et al. | 378/207 |
| 4,225,789 | 9/1980 | Albrecht | 378/207 |
| 4,319,184 | 3/1982 | Kowalczyk | 333/81 R |
| 4,352,020 | 9/1982 | Horiba et al. | 378/207 |
| 4,399,550 | 8/1983 | Hauck et al. | 378/5 |
| 4,367,409 | 1/1983 | Klausz | 250/385 |
| 4,411,012 | 10/1983 | Pfeiler et al. | 378/17 |
| 4,497,061 | 1/1985 | Hounsfield | 378/207 |
| 4,510,577 | 4/1985 | Tsujii et al. | 378/54 |
| 4,571,491 | 2/1986 | Vinegar et al. | 378/207 |
| 4,626,688 | 12/1986 | Barnes | 378/156 |
| 4,709,382 | 11/1987 | Sones | 378/5 |

OTHER PUBLICATIONS

Fenster, A., "Spilt Xenon Detector for Tomochemistry in Computed Tomography," Jour. of Computer Assisted Tomography, 2:243–252, Jul. 1978, Raven Press, New York.

Primary Examiner—Janice A. Howell
Assistant Examiner—John C. Freeman
Attorney, Agent, or Firm—Watts, Hoffmann, Fisher & Heinke Co.

[57] ABSTRACT

An apparatus and method is disclosed for facilitating calibration of a dual energy digital radiography system having a focused multi-element detector assembly. The apparatus includes two sets of calibration elements, each set made of a different basis material. Each calibration element defines a segment of an annulus and is positionable between the system source and detector such that the center defined by the annulus is substantially coincident with the focal spot of the source. Within individual sets, the thicknesses of the respective member elements differ one from another in accordance with a binary progression. Each of the calibration elements is positioned and sized such that it intercepts and attenuates all radiation which ultimately falls upon the detector.

9 Claims, 5 Drawing Sheets

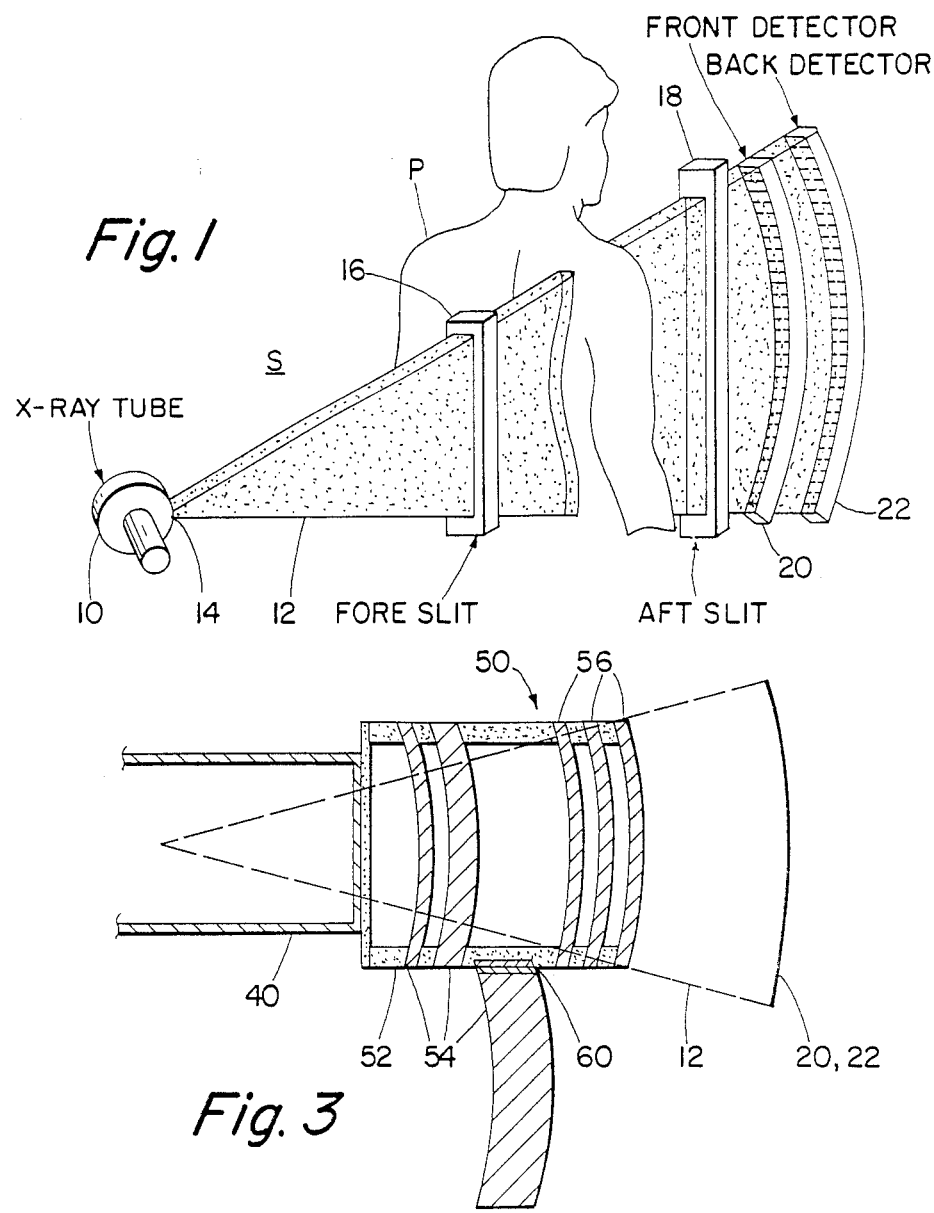
Fig. 1
Fig. 3
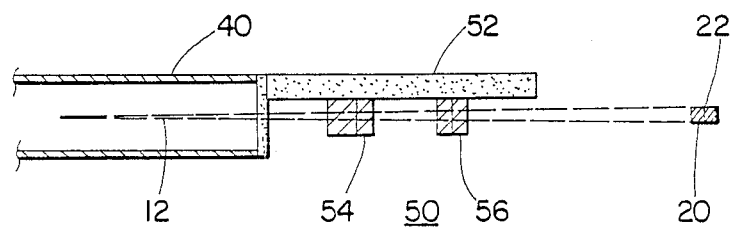
Fig. 4

RADIATION IMAGING CALIBRATION

This application is a continuation of application Ser. No. 798,427, filed 11/15/85.

TECHNICAL FIELD

This invention relates to the field of medical diagnostics, and more particularly to an improved method and apparatus for use in calibration of dual energy digital radiography.

BACKGROUND ART

In a conventional radiography system, an x-ray source is actuated to direct a divergent area beam of x-rays through a patient. A cassette containing an x-ray sensitive phosphor screen and light and x-ray sensitive film is positioned in the x-ray path on the side of the patient opposite the source. Radiation passing through the patient's body is attenuated in varying degrees in accordance with the various types of tissue through which the x-rays pass. The attenuated x-rays from the patient emerge in a pattern, and strike the phosphor screen, which in turn exposes the film. The x-ray film is processed to yield a visible image which can be interpreted by a radiologist as defining internal body structure and/or condition of the patient.

More recently, digital radiography techniques have been developed. In digital radiography, the source directs x-radiation through a patient's body to a detector in the beam path beyond the patient. The detector, by use of appropriate sensor means, responds to incident radiation to produce analog signals representing the sensed radiation image, which signals are converted to digital information and fed to a digital data processing unit. The data processing unit records and/or processes and enhances, the digital data. A display unit responds to the appropriate digital data representing the image to convert the digital information back into analog form and produce a visual display of the patient's internal body structure derived from the acquired image pattern of radiation emergent from the patient's body. The display system can be coupled directly to the digital data processing unit for substantially real time imaging, or can be fed stored digital data from digital storage means such as tapes or discs representing patient images from earlier studies.

Digital radiography includes radiographic techniques in which a thin fan beam of x-rays is used. In this technique, often called "scan (or slit) projection radiography" (SPR) a fan beam of x-rays is directed through a patient's body. The fan is scanned across the patient, or the patient is movably interposed between the fan beam x-ray source and an array of individual cellular detector segments which are aligned along an arcuate or linear path. Relative movement is effected between the source-detector arrangement and the patient's body, keeping the detector aligned with the beam, such that a large area of the patient's body is scanned by the fan beam of x-rays. Each of the detector segments produces analog signals indicating characteristics of the received x-rays.

These analog signals are digitized and fed to a data processing unit which operates on the data in a predetermined fashion to actuate display apparatus to produce a display image representing the internal structure and/or condition of the patient's body.

One of the advantages of digital radiography is that the digital image information generated from the emergent radiation pattern incident on the detector can be processed, more easily than analog data, in various ways to enhance certain aspects of the image, to make the image more readily intelligible and to display a wider range of anatomical attenuation differences.

An important technique for enhancing a digitally represented image is called "energy subtraction".

Energy subtraction exploits energy-related differences in attenuation properties of various types of tissue, such as soft tissue and bone, to derive a material-specific image, mapping substantially only a single material in the body.

It is known that different tissue, such as soft tissue (which is mostly water) and bone, exhibit different characteristics in their capabilities to attenuate x-radiation of differing energy levels.

It is also known that the capability of soft tissue to attentuate x-radiation is less dependent on the x-ray's energy level than is the capability of bone to attenuate x-rays. Soft tissue shows less change in attenuation capability with respect to energy than does bone.

This phenomenon enables performance of energy subtraction. In practicing that technique, pulses of x-rays having alternating higher and lower energy levels are directed through the patient's body. When a lower energy pulse is so generated, the detector and associated digital processing unit cooperate to acquire and store a set of digital data representing the image produced in response to the lower energy pulse. A very short time later, when the higher energy pulse is produced, the detector and digital processing unit again similarly cooperate to acquire and store a set of digital information representing the image produced by the higher energy pulse.

In early energy subtraction techniques, the values obtained representing the lower energy image were then simply subtracted from the values representing the higher energy image.

Since the attenuation of the lower energy x-rays by the soft tissue is about the same as the attenuation of the higher energy x-rays, subtraction of the lower energy image data from the higher energy image data approximately cancels out the information describing the configuration of the soft tissue. When this information has been so cancelled, substantially all that remains in the image is the representation of bone. In this manner, the contrast and visibility of the bone is substantially enhanced by energy subtraction.

Details of energy subtraction techniques in digital radiography and fluoroscopy are set forth in the following technical publications, all which are hereby incorporated specifically by reference:

Hall, A. L. et al: "Experimental System for Dual Energy Scanned Projection Radiology". *Digital Radiography* proc. of the SPIE 314: 155–159, 1981;

Summer, F. G. et al: "Abdominal Dual Energy Imaging". *Digital Radiography* proc. SPIE 314: 172–174, 1981;

Blank, N. et al: "Dual Energy Radiography: a Preliminary Study". *Digital Radiography* proc. SPIE 314: 181–182, 1981; and Lehman, L. A. et al: "Generalized Image Combinations in Dual kVp Digital Radiography", *Medical Physics* 8: 659–667, 1981.

The above incorporated article by Lehman, et al describes more recently conceived techniques for modifying the above described simple subtraction technique to enhance the quality of the energy subtracted image.

It has been proposed in energy subtraction to utilize a particular type of dual energy detector assembly which can produce separate signals representing each of lower and higher x-ray energy incident on the dectector. Such a detector assembly enables the practice of energy subtraction without the necessity for switching kVp x-ray output levels, or employing other means for periodically attenuating the x-ray beam, such as rapid interposition and removal of a filter to and from the x-ray path. Such a detector employs a dual layer of phosphor-detector elements, wherein the phosphor material of a first, or front, layer preferentially responds to energy of a relatively lower energy value. A second, or rear, detector layer preferentially responds to x-ray energy in a higher range. Such a detector, and its method of use, is described in published European Patent Application No. 83307157.4 published on Aug. 8, 1984 by Gary T. Barnes, which published application is hereby expressly incorporated by reference.

Since dual energy techniques can produce material-specific images, wherein substantially only bone, or substantially only soft tissue, are imaged, calibration of the system is desirably performed for both bone and soft tissue, i.e., for both low and high energy response. In doing this, it is known to use portions of aluminum to simulate radiation attenuation characteristics of bone, and to use portions of acrylic to simulate attenuation characteristics of soft tissue.

Prior art calibration techniques include interposition in the x-ray path, between the source and the detector, of various combinations of thicknesses of acrylic and aluminum in sets of different thickness combinations, actuating the source and monitoring the system output in the presence of the various combinations to determine how the imaging system response depends on the various acrylic/aluminum thickness combinations.

Two basic approaches to dual energy calibration have been proposed. A sequence of images may be taken with different thickness combinations of acrylic and aluminum covering the entirety of each image. Another proposal has been that only a single image be taken, but that image contains, in a number of different discrete regions, representations of several different acrylic/aluminum thickness combinations. Also, use of various step wedges has been proposed, wherein one device includes several different thickness combinations, distributed among respective areas, for performing calibration in accord with the latter of the above indicated proposals. The portions of acrylic and aluminum define surfaces parallel to the plane of the detector.

One problem with the prior art calibration apparatus is that the distance the x-rays travel through the acrylic or aluminum varies slightly with the angle of the path of the x-rays with respect to the detector and calibration material. Regions of the image toward the boundary of the detector receive somewhat less radiation, because rays incident on those outer regions travel a somewhat longer distance through the attenuating calibration material. This phenomenon gives rise to an inaccurately nonuniform calibration result.

Where only one exposure is made, and different regions of the same image are attenuated with differing aluminum/acrylic thickness combinations, averaging techniques, useful in minimizing the effect of individual detector element nonuniformity in calibration, are less effective, inasmuch as only the detector elements corresponding to the portion of the image attenuated by a particular acrylic/aluminum thickness combination are susceptible of averaging.

Where different regions are attenuated differently in making a calibration image, edge effects of the radiation interacting with the various calibration elements sometimes adversely affect uniformity and accuracy of response and reliability of the calibration technique.

Also, a large number of calibration element thicknesses of aluminum and acrylic are required, in order to perform calibration at a relatively large number of calibration points for both soft tissue and bone attenuation.

Calibration elements must be very carefully machined so that their effect on radiation is precisely predictable. Where complex shapes, such as step wedges, are used for calibration elements, the cost of machining can be considerable.

Since it is desirable to calibrate with a large number of combinations of acrylic/aluminum thicknesses, calibration can be quite time consuming due to the need for manually placing, removing and replacing combinations of calibration elements in the x-ray beam.

It is an object of the present invention to provide a light weight, inexpensive and accurate calibration apparatus and method wherein all x-rays traverse paths of equal length in penetrating the apparatus.

The present invention will be more fully understood by reference to the following detailed description, and to the drawings, in which:

DISCLOSURE OF THE INVENTION

The disadvantages of the prior art are reduced or eliminated by employment of an improved calibration apparatus and method.

The apparatus of this invention is employed in a radiation imaging system comprising a source defining a focal spot from which penetrative radiation primarily emanates upon actuation of the source. The system also includes a radiation detector spaced from the source and positioned to receive x-rays emanating from the focal spot. The calibration apparatus includes a calibration element comprising radiation attenuating material interposable between the source and detector, the calibration element being configured to describe or define a substantially curved geometry. More specifically, the curved geometry of the calibration element defines an arc which is substantially centered at the focal spot.

By implementation of such an arcuate calibration element, the path of all x-rays penetrating the element is substantially equal, where the element has a uniform thickness. This configuration thus avoids errors otherwise introduced where the path lengths of x-ray travel through the radiation attenuating material differ with the angle of the x-rays. Accordingly, errors in calibration due to this phenomenon are diminished.

A calibration element configured as described above is particularly useful with a focused detector, wherein the detector possesses a curvature also defining an arc which is approximately concentric with the x-ray source focal spot.

In another embodiment, the calibration element is sufficiently broad to intercept and attenuate all radiation which reaches the elements of the detector. This feature facilitates detector response averaging and energy dependent gain correction.

In accordance with another embodiment, a radiation imaging system is provided comprising an x-ray source for projecting a beam of x-rays and an x-ray detector spaced from the source. Mechanical means is included and coupled to the detector for causing detector motion along a path. A calibration element is provided, along with means for coupling the calibration element for motion synchronous with that of the detector.

This embodiment of the invention enables given detector elements of the detector to "see" only x-rays passing through the same portion of the calibration element. It thus reduces the effect of non-uniformities in configuration of the calibration element, and of inhomogeneities in the material of which the calibration element is made.

Another embodiment of the invention comprises a slit projection radiation imaging system including a source for propagating a beam of penetrative radiation, means for collimating the radiation beam into a relatively thin fan beam and a detector of penetrative radiation interposed in the beam. A calibration element is interposed between the collimation means and the detector, the calibration element being interposed in the beam and presenting to the beam an area approximately congruent with the cross sectional geometry of the beam at the location of the calibration element.

Implementation of this embodiment of the invention minimizes the mass and size of the calibration apparatus by restricting the amount of material to only that necessary to cover or intercept the entire x-ray beam.

In accordance with a further embodiment, a radiation imaging system includes a source for propagating a penetrative radiation beam and a penetrative radiation detector. Interposable between the source and detector are members of a set of calibration elements each capable of attenuating penetrative radiation to a different degree, the degrees of radiation attenuation capability differing among the elements of the set in accordance with a binary progression.

This feature of the invention provides for maximization of the number of different combinations of attenuation that can be achieved by the use of a predetermined number of combinations of calibration elements, while assuring that the various attenuations available by use of the combinations are distributed in a linear progression from zero to the maximum obtainable by the use of all the elements.

In another embodiment, the thicknesses of the elements differ one from another in accordance with a binary progression.

In accordance with another embodiment, the calibration elements comprise fluid-tight envelopes interposable in the x-ray beam between a source and a detector. The fluid-tight envelopes each define an arcurate volume having a center approximately coincident with the focal spot of the x-ray source.

By use of such envelopes, liquids of gases may be used as radiation attenuating material. Water is an attenuating material roughly equivalent to soft tissue. Higher energy attenuation can be obtained by the use of xenon gas.

Fluid-tight envelopes containing gas can be employed as multiple density radiation attenuators by the use of apparatus to regulate the pressure of the gas within the envelope. As the pressure increases, the attenuating capability of the gas also rises. In this way, a series of calibration measurements at different radiation attenuating levels can be accomplished by the use of a single hollow calibration element.

Brief Description Of Drawings

FIG. 1 is a perspective drawing illustrating a portion of an imaging system in connection with which the present invention is implemented;

FIG. 3 is a cross-sectional view illustrating a portion of the inventive subject matter;

FIG. 4 is a plan view illustrating the portion shown in FIG. 3;

BEST MODE FOR CARRYING OUT INVENTION

Figure 2:
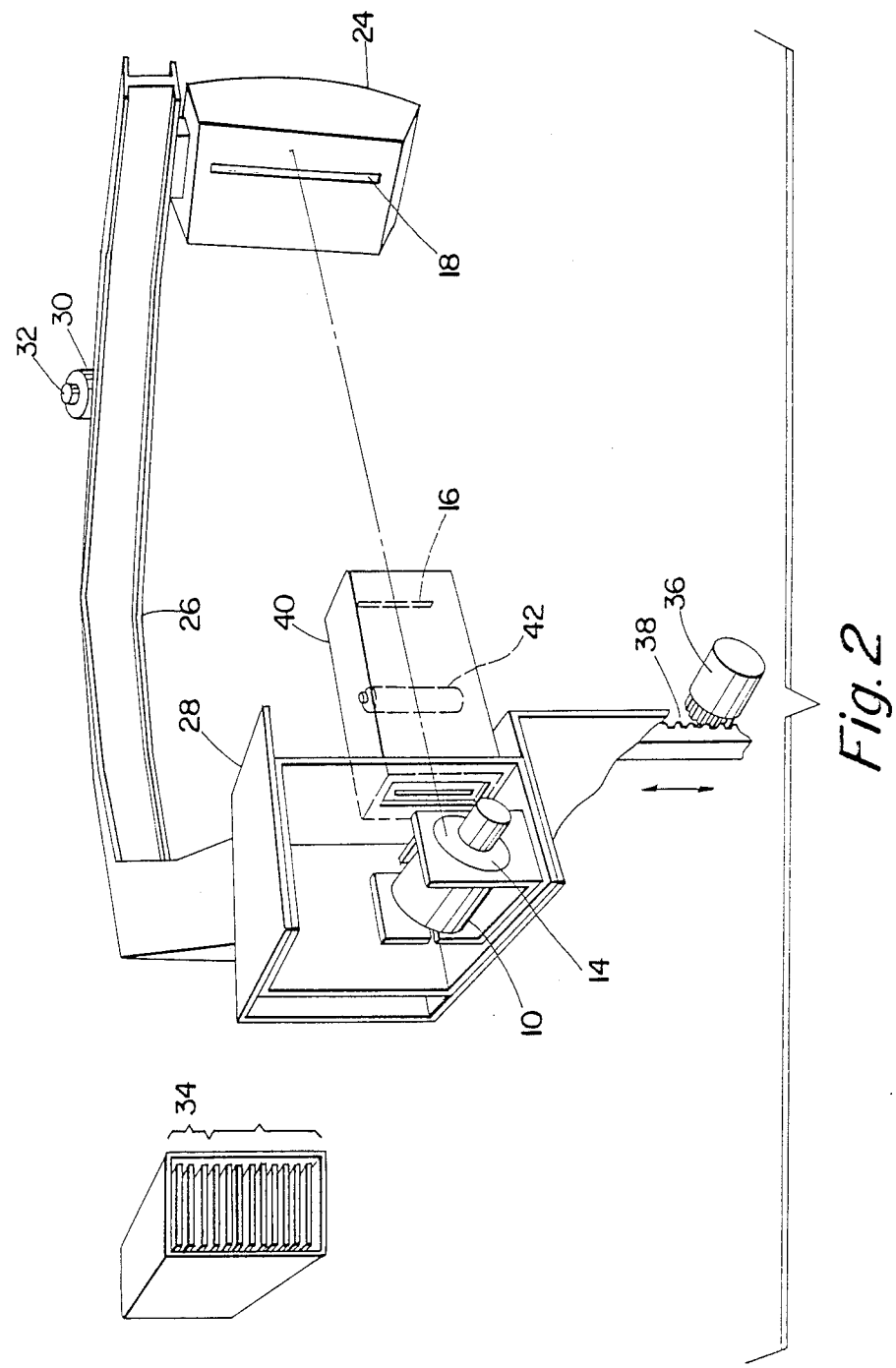
FIG. 2 is a perspective view illustrating mechanical components of the system of FIG. 1.

The present invention is described as implemented in a slit projection dual energy digital radiography system S as illustrated in FIGS. 1 and 2. The present invention comprises a calibration phantom apparatus for use in calibrating performance of the system S. The calibration phantom comprises a set of reference objects which, when radiographed, permit absolute calibration of a dual energy system. Techniques for calibration of a dual energy radiographic system are described in detail in the above incorporated article by Lehmann, et al., and also Wong, C. K., et al "Calibration Procedure in Dual-Energy Scanning Using the Basis Function Technique" *Medical Physics* 10(5) 1983, which is also expressly incorporated by reference.

With reference to FIG. 1, the system S includes an x-ray tube 10 and associated power circuitry (not shown) for actuating the tube to produce and propagate a beam of x-rays indicated generally at 12. The x-rays emanate primarily from a focal spot 14 associated with the x-ray tube. The x-ray beam 12 is collimated into a thin fan by a first collimator element 16, after which the fan passes through a patient P. The emergent beam is again collimated by a second collimator 18, and falls incident upon a focused dual layer detector comprising detector layers 20, 22.

The dual layer detector is of a type described in the above incorporated European patent application by Barnes. As stated in that document, the detector layer 20 responds preferentially to lower energy radiation, while the detector layer 22 responds preferentially to higher level radiation. Thus, the detector comprising layers 20, 22 can produce dual energy data simultaneously.

The detector is of the focused variety, in that each layer 20, 22 comprises a row of adjacent individual detector elements which are arranged along a curvilinear path comprising an arc which is concentric with the focal spot 14 of the x-ray tube. As shown in FIG. 1, the orientation of the x-ray fan beam 12 and of the detector layers 20, 22 is in a substantially vertical plane.

The general construction and attributes of the digital radiographic imaging system S are set forth in the following publication, which is hereby expressly incorporated by reference: Tesic, M. M., et al, "Digital Radiography of the Chest: Design Features and Considerations for a Prototype Unit", *Radiology*, Vol. 148 No. 1 pgs. 259-264, July, 1983.

Mechanical aspects of the system S are illustrated in FIG. 2. A detector module 24 encloses the detector layers 20, 22, and defines the collimator element 18 in the form of a slot. The detector module is supported upon an arm 26 which is mounted to base structure 28 for pivotal movement about a vertical axis extending through the focal spot 14 of the x-ray tube 10.

A gear motor 30 is coupled mechanically to drive the arm 26 in motion about its vertical pivot axis aligned with the x-ray tube focal spot 14. An encoder 32 senses the position of the arm 26 about its path of rotation, and communicates that position to control electronics 34.

A second gear motor 36 is coupled by means of a rack and pinion linkage 38 to controllably impart vertical adjustment movement to the arm and detector module.

A gantry collimator housing 40 encloses the structure defining the collimator element 16 and moves with the arm 26 such that the collimator element 16, and the beam 12, remains continuously aligned with the element defined by the slot 18 in the detector module 24. The gantry collimator housing also encloses a beam filter 42.

As is described in more detail below, the calibration phantom apparatus associated with the present invention is, in use, mounted to the end of the gantry collimator housing 40 which faces the detector module.

The system S scans the x-ray fan beam across the patient's body about he vetical axis to which pivotal motion of the arm 26 is restrained. The beam is scanned across the patient's chest and the emergent beam is detected. Information represented by the detected x-rays is processed and displayed to illustrate a representation of an image of the patient's internal body structure or condition.

More specifically, the mechanical linkage illustrated in FIG. 2 scans the collimator elements 16, 18, and the detector module, in unison, maintaining alignment between the x-ray beam, collimator elements and detector at all times throughout the scanning rotative motion described above.

During scanning, analog detector outputs from each of the detector elements are periodically sampled. Each sampling produces analog signals representing a portion of image information. Over the course of the scan from one side to the other side, signals are developed describing a plurality of image lines, which together constitute an area image of the patient's internal body structure.

The analog signals are digitized and processed in known fashion to construct a digital representation of an image of the patient's internal body structure scanned by the x-ray beam on a pixel-by-pixel basis. Digital signals are then converted to analog form and displayed on a monitor (not shown).

Digital storage means (not shown) can be provided in conjunction with the system in order to digitally store image representations for future use. In such event, the digitally stored signals are later played back, and converted to analog form from which their corresponding images are displayed.

Elevational and plan views of one embodiment of the present invention are given in FIGS. 3 and 4, respectively.

FIG. 3 illustrates one embodiment 50 of a collimator phantom apparatus having a frame portion 52 which is bolted in known fashion to the end of the gantry collimator housing 40 which faces the detector module. Two sets 54, 56 of arcuate shaped portions of calibration material are mounted to the frame 52 in such a way that they can be positioned to intercept the x-ray fan beam 12. Each of the arcuate calibration elements may be easily swung in or out of the fan beam on hinges, such as shown for example at 60.

The arcuate calibration elements each define an arc which, when the element is positioned to intercept the x-ray beam, the arc is substantially concentric with the focal spot of the x-ray tube 10, and can thus be said to be "focused" on the tube focal spot. Also, each arcuate calibration element is machined to have a precisely uniform thickness, in directions radial with respect to the focal spot.

The geometry of the arcuate calibration elements is important. More specifically, each element is a section of an annulus centered on the x-ray tube focal spot. All x-ray paths from the focal spot to the detector thus traverse equal amounts of calibration material. Hence, all detector elements "see" the same thickness of calibration material.

A significant feature of this invention resides in the fact that each of the focused calibration elements defines an expanse of material which is sufficient to intercept all the x-rays from the source which travel along paths such that they are ulitmately incident upon the detector. Thus, the focused calibration elements can be said to "cover" the entire multi-element detector.

Since the calibration phantom frame 52 is physically ganged to the gantry collimator, an individual detector element is "covered" by the same area of the calibration material during an entire calibration scan. This minimizes errors due to any non-uniformities in the thickness and material composition of the arcuate calibration elements. Also, the size and weight of the calibration phantom is reduced from what would be necessary if the full scan area had to be covered simultaneously by the calibration elements. The arcuate calibration elements need be only slightly wider, in a direction tangential to scanning motion, than the fan beam itself, which is itself in the neighborhood of one millimeter in width.

Figures 5, 6:
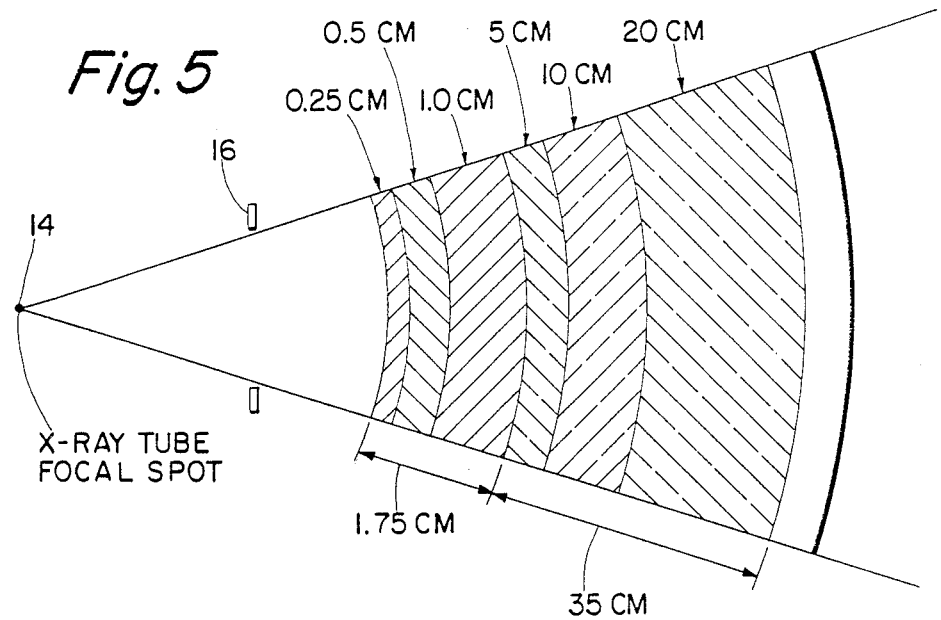
FIG. 5 is a detailed cross-sectional elevational view illustrating detail of the portion shown in FIG. 3.
FIG. 6 is a tabular representation illustrating a manner of use of an embodiment of the present invention.

Preferably, each arcuate calibration element is made of either acrylic or aluminum. FIG. 5 illustrates (not to scale) typical preferred thicknesses for the arcuate calibration elements and indicates the composite thicknesses which can be attained through combinations. For example, three acrylic arcuate calibration elements provide eight thickness combinations. Moreover, if the three arcuate calibration elements have a binary thickness progression, then the eight combinations of thicknesses possess a simple, uniform distribution of possible total thicknesses from zero to the maximum thickness attainable by positioning all three elements to intercept the x-ray beam.

While acrylic and aluminum are preferable materials, theoretically any two different materials could be used to effect calibration. For example, a liquid such as water could be used. As described below in more detail, certain gases can be effective as calibration materials. Portions of calcium itself could be machined to constitute calibration elements corresponding to bone attenuation. These are only a few examples, and the invention should be construed as encompassing the use of all suitable materials.

While the preferred embodiment calls for the thicknesses of the calibration elements to differ one from another in accordance with a binary progression, the invention also encompasses defining the thicknesses of the respective calibration elements within a set as having a progression such that the radiation attenuating capabilities, rather than the thicknesses, of the calibration elements, correspond to a binary progression. Note in this connection that the actual attenuating capability of a portion of radiation attenuating material varies as an approximation of an exponential function with respect to thickness.

As described in more detail below, the preferred embodiment of this invention includes two sets of focused calibration elements, one set being made of acrylic, the other set being made of aluminum. For purposes of clarity, it is emphasized that the binary progressions of thicknesses or radiation attenuating capability are established only within individual sets of said elements which are made of like material. It is not necessary that the binary progression of thickness or radiation attenuating capability be observed integrally over both sets considered as a whole.

In fact, the aluminum calibration elements will be generally much thinner than the acrylic calibration elements. Tests have shown that a suitable range of thicknesses for the aluminum calibration elements is from 0 to 3 centimeters, while suitable thicknesses of acrylic range from 0 to about 30 centimeters.

Consider N acrylic arcuate calibration elements numbered (in order of increasing thickness) from zero to N−1. Let T (I) be the thickness of the Ith element, and assume the thicknesses form a binary sequence. Then, $$T(I)=(2^N)T(0).$$

By combining the arcuate calibration elements one can obtain $2^N$ different thicknesses from zero to $[(2^N)-1]T(0)$ with a uniform increment of T(0).

The calibration phantom frame must be accurately aligned with the x-ray fan beam, so that the fan beam does not "miss" the relatively narrow arcuate calibration elements. This is accomplished by using adjustable, threaded standoffs coupled in known fashion between the frame 52 and the gantry collimator housing 40.

Installing and removing the frame 52 from the housing 40 is simple and convenient. The design insures that, once aligned, the frame can be repeatedly removed and reinstalled without need for further alignment.

In the apparatus of FIG. 3, the set of arcuate calibration elements 54 comprise acrylic, and the set 56 comprise aluminum. The acrylic material has radiation attenuation characteristics resembling those of soft tissue, which is mosly water, while the aluminum has radiation attenuation characteristics resembling bone.

Calibration involves making detector measurements with various combinations of the arcuate calibration elements positioned to intercept the x-ray fan beam 12.

In operation, a predetermined combination of arcuate calibration elements is interposed in the x-ray fan beam, and exposure is made using the digital radiography system, as though a patient were present. Data from the exposure, generated by the detector layers 20, 22, are stored. The process is repeated for other combinations of interposed arcuate calibration elements, and the results plotted and/or compared in order to evaluate how the system responds to various combinations of simulated bone and simulated soft tissue. Both the low energy level and high energy level responses of the detector are separately evaluated. Details of known methods for collecting and evaluating calibration data are set forth in the above incorporated publications by Lehmann and Wong. Such techniques are often called "basis" calibration, and the aluminum and acrylic materials used in the calibration elements are often called "basis materials".

In evaluating calibration test results, it is preferable during dual energy calibration to average together the responses of many elements from the layer 20 and of many elements from the layer 22, respectively. Averaging reduces errors due to noise, and prevents anomalous elements from strongly biasing the measurements. Thus, averaging improves the accuracy with which the dual layer array response functions can be determined.

In order for averaging to be effective, each element included in the averaging must "see" the same thickness combination of calibration material. This is why the focused image detector ideally requires similarly focused calibration elements.

It is also advantageous that all the elements, not just some, be included in the basis calibration measurements.

The calibration phantom of the present invention covers the entire detector with uniform thicknesses of calibration attenuation material and provides equal length ray paths through the calibration material to each point of the detector. This feature simplifies the structure and facilitates averaging of all detector elements of a particular layer.

The advantages of the present calibration phantom covering the entire multi-element detector are not limited to the context of averaging discussed above. Recently, there has been developed a technique called energy dependent gain correction to deal with non-uniform response of detector elements. This method requires that the response of each element be measured as a function of acrylic/aluminum thickness combinations. A correction function is then generated for each element which maps that element's response into the response that a "nominal" ideal element would give. In order to correct the response of all the elements, they must all participate simultaneously in the basis calibration measurements. Details of an energy dependent gain correction technique are set forth in a patent application filed concurrently herewith, serial number to be assigned, by Sones et al., entitled "Energy Dependent Gain Correction for Radiation Detection", assigned to the assignee of the present invention, which is hereby expressly incorporated by reference.

Another advantage afforded by the present invention is its relative simplicity. With only a few calibration elements, one can, by use of the present invention, obtain a large number of different basis material combinations. For example, just three acrylic elements and three aluminum elements provide the possibility of 64 different combinations. See, for example, the tabulation of FIG. 6.

Moreover, the binary thickness sequence insures that the thickness combinations are distributed uniformly from minimum to maximum acrylic and aluminum thicknesses. Again, refer to FIG. 6.

The quality of a basis calibration is only as good as the accuracy of the calibration phantom. The calibration phantom must be precisely machined. Complex calibration phantoms, such as crossed step-wedges, are difficult to machine accurately, and are expensive. Arcuate calibration elements, such as those described here, are, on the other hand, simple to machine and relatively inexpensive.

Other embodiments of the invention are possible. For example, the calibration phantom frame 52 can be attached to a stationary portion of the system gantry instead of to the gantry collimator housing 40, which moves in unison with the arm 26. During calibration, the source/detector assembly is moved to a central scan position aligned with the calibration phantom 50 in its stationary position, and data are taken in stationary mode. This approach has the advantage of not requiring the gantry collimator housing 40 to support the cantilevered weight of the calibration phantom 50.

Other means besides the hinges such as shown at 60 can be provided to facilitate installation and removal of the calibration elements to and from the x-ray beam. For example, known types of detents, or snaps, with associated guide pins to accurately locate the calibration elements, can be used.

Figure 7:
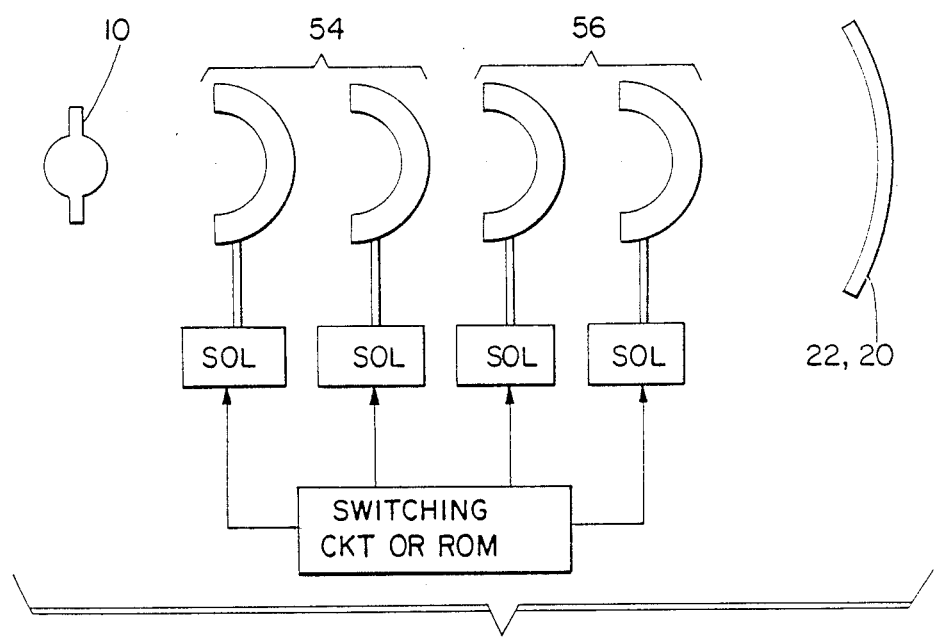
FIG. 7 is a view illustrating a mode of use of the invention in accordance with another embodiment.

Additionally, it is considered advantageous in some applications to provide for automatic and/or mechanized means of inserting and removing the individual calibration elements in and out of the fan beam, in known fashion, such as by the use of known electric solenoids and appropriate switching equipment. A basis calibration routine could be easily derived from the above publications by Lehmann and Wong, and the system programmed to successively execute the proper interposition of calibration element thicknesses in accordance with that routine. Basis calibration can be a lengthly procedure (especially if a large number of acrylic/aluminum combinations are used) and such an automated system could alleviate operator tedium and error in manually changing the calibration thickness (See FIG. 7).

The basis materials used for the arcuate calibration elements need not be acrylic and aluminum. Acrylic and aluminum are convenient choices because they are readily available, easy to machine, and their x-ray attenuation characteristics approximate water and bone, respectively. It may be advantageous to select materials which more exactly mimic water and bone.

In accordance with a further embodiment, the calibration material can comprise a liquid or a gas.

Figure 8:
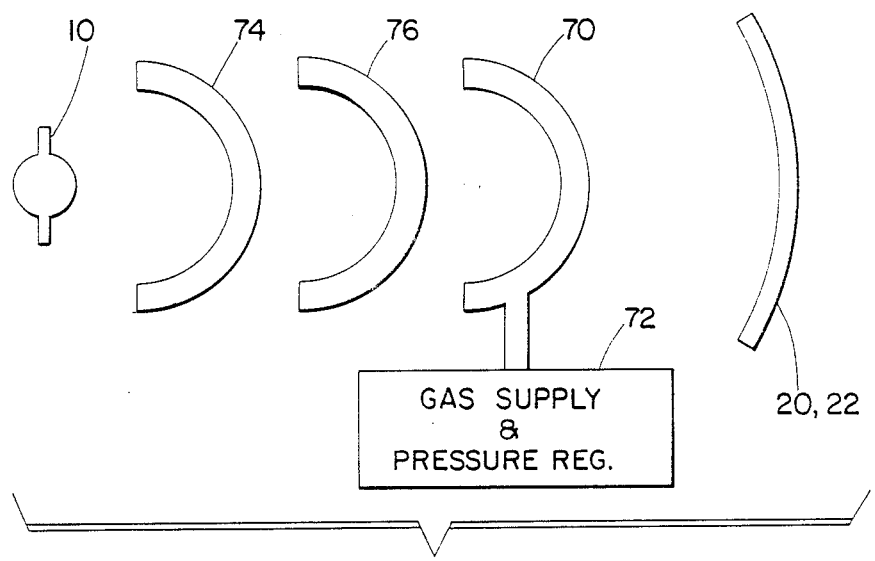
FIG. 8 is a diagram illustrating a further embodiment of the invention.
Figure 9:
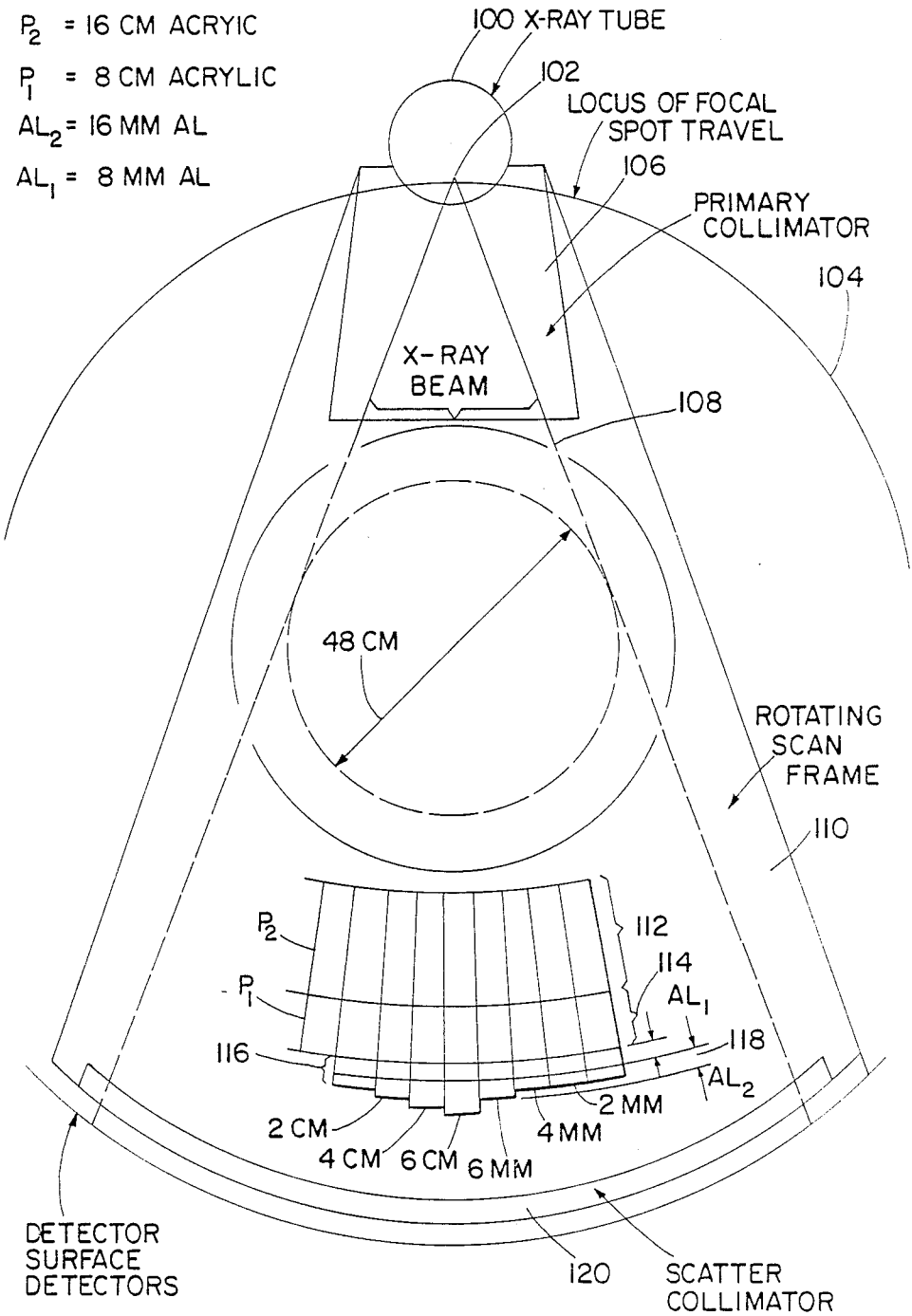
FIG. 9 is an elevational view illustrating components and geometry of a specific embodiment of the present invention.

For example, a gas can be used to simulate radiation attenuation attributable to bone. In accordance with such an embodiment, a calibration element for attenuating radiation takes the form of a hollow, substantially gas-tight envelope 70 which defines an interior volume geometrically defining a segment of an annulus. The gas to be used in attenuating radiation is injected into the envelope 70. FIG. 8 illustrates a known type of pressure adjusting apparatus 72 which is coupled to a supply of the gas used for attenuating radiation. The pressure regulating apparatus 72 provides for controlled adjustment of the gas pressure within the envelope 70, and hence can control the density of the gas within that envelope. The envelope 70 and associated pressure regulating apparatus 72 can be used to replace the plurality of aluminum calibration elements described above. In accordance with such an embodiment, changes in radiation attenuating capabilities are effected by adjusting the gas pressure within the envelope 70, in a manner analogous to the adjustment of radiation attenuating capabilities by interposing different thicknesses of aluminum in the beam path, as described above.

As mentioned above, liquid can also be used as an attenuation material in the practice of this invention. FIG. 8 illustrates two additional hollow, substantially liquid-tight envelopes 74, 76, each defining an interior volume comprising a segment of an annulus. The envelopes 74, 76 are interposable in and out of alignment with the envelope 70. The respective thicknesses of the annular segments defined within the envelopes 74, 76 differ in accordance with a binary progression. The liquid within the envelopes 74, 76 is chosen to have radiation attenuating characteristics similar to that of soft tissue. Water is an appropriate liquid. Note that, because fluids are substantially incompressible, the pressure regulating apparatus 72 cannot advantageously be used in connection with liquid filled envelopes such as 74, 76.

A suitable gas for attenuating radiation passing through the envelope 70 comprises xenon.

In accordance with another embodiment, one or more of the curved calibration elements can comprise a section of a sphere. Such an embodiment would be useful in conjunction with a three dimensional focused detector, such as is described in patent application Ser. No. 673,779 filed Nov. 21, 1984 by Sones, et al., and entitled "Focused Detector", and assigned to the assignee of this application, which is hereby expressly incorporated by reference. In the instance of such a spherical area detector and accompanying spherical section shaped calibration elements, all portions of the detector would "see" the same thickness of calibration material.

It also within the scope of this invention that the arcuate calibration elements includes a high density radiation absorbing material, such as lead, at the outer boundary of each element. This absorber reduces the amount of radiation that is scattered, thereby reducing errors in calibration. Referring to FIG. 4, a calibration element 56 is illustrated in cross section, with a relatively thin layer of lead 57 extending about its outer boundaries.

It is to be understood that the foregoing disclosure of embodiments of the present invention is intended as illustrative, rather than exhaustive, of the invention. Those of ordinary skill in the relevant art may make additions or modifications, or deletions from, the specific embodiments described herein without departing from the spirit or scope of the invention, as defined in the appended claims.

We claim:

1. A calibration apparatus for an x-radiation imaging system including an x-ray source and a detector of x-ray energy spaced from the source, said calibration apparatus comprising:
   (a) a first substantially sealed envelope of a first uniform thickness interposable between and distinct from each of the source and detector;
   (b) a second substantially sealed envelope interposable between and distinct from each of the source and detector and defining a volume having a second thickness different from said first thickness, and
   (c) first and second apparatus means having structure for injecting gas into said substantially sealed envelopes and for adjusting the respective pressures of said gas within said respective envelopes.

2. An x-ray imaging system comprising:
   (a) a source of x-rays, said source defining a focal spot from which x-radiation primarily emanates upon actuation of said source;
   (b) an x-ray sensitive radiation detector spaced from said source;
   (c) a substantially sealed calibration element comprising an envelope positionable in said x-rays and distinct from said source and from said detector, said envelope defining an annular volume oriented with the center defined by said annular volume substantially coinciding with said focal spot;

(d) apparatus means to supply a quantity of gas to said envelope, and (e) means controlling the pressure of the gas within said envelope.

3. A projection x-ray imaging system comprising:

(a) a source of x-rays, said source defining a focal spot from which x-radiation primarily emanates upon actuation of the source;

(b) a collimator for shaping the x-rays into a relatively thin fan beam;

(c) an x-ray sensitive dual energy radiation detector spaced from said source and interposed in the path of said beam;

(d) a substantially sealed basis calibration element comprising an envelope positionable in said x-rays and distinct from said source and from said detector, said envelope defining an annular volume oriented with the center defined by said annular volume being substantially coincident with said focal spot;

(e) apparatus to supply a quantity of gas to said envelope;

(f) apparatus for adjustably controlling the pressure of the gas within said envelope;

(g) apparatus for scanning said fan beam, said envelope and said detector synchronously about said focal spot and in a direction substantially perpendicular to the plane defined by said fan beam, and (h) circuitry coupled to said detector for producing a representation of a shadowgraphic image of a pattern of x-rays distributed about a two dimensional field of view defined by a surface generally normal to the direction of x-rays when propagated along said path toward said detector.

4. A projection radiation imaging system comprising:

(a) a source for propagating a beam of x-rays and defining a focal spot from which x-rays primarily emanate to be propagated along a path;

(b) structure for collimating the x-radiation beam into a relatively thin fan beam generally defining a plane;

(c) a dual energy two layer x-ray detector spaced from said source;

(d) a plurality of curved basis calibration elements, each calibration element being of substantially uniform thickness and defining an arc;

(e) apparatus for mounting said plurality of calibration elements for adjustable movement into and out of said x-ray beam at respective locations between said collimator and said detector;

(f) apparatus for scanning said detector and said calibration elements, along with said fan beam, in unison, in a direction substantially perpendicular to the plane defined by the fan beam;

(g) circuitry coupled to said dual energy detector for producing a dual energy representation of a shadowgraphic image corresponding to a pattern of x-rays distributed over a two dimensional field of view which is defined by a surface which is generally normal to the direction of propagation of x-rays along said path.

5. A scan projection x-ray radiation calibration apparatus comprising:

(a) a frame;

(b) a first set of x-ray radiation attenuating calibration elements;

(c) means for mounting each element of said first set to said frame for movement with respect to said frame;

(d) said elements of said first set being comprised of substantially the same kind of material and each of said elements of said first set defining an annulus, the thicknesses of each one of said elements being uniform, said thicknesses differing from one element to another in accordance with a binary progression, and;

(e) a second set of x-ray radiation attenuating calibration elements mounted on said frame for movement with respect to said frame, said second set of elements each being of uniform thickness and defining an arc, and having thicknesses varying from one element to another in accordance with a binary progression.

6. The apparatus of claim 5, wherein said material comprises a liquid.

7. The apparatus of claim 5, wherein said material comprises a gas.

8. A scan projection radiographic imaging system comprising:

(a) an x-ray source defining a focal spot from which x-radiation primarily emanates upon actuation of the source in a generally planar fan shaped beam;

(b) a generally elongated x-ray detector array spaced from the source and positioned to receive x-rays emanating from said source, said detector array also being curved about an axis substantially perpendicular to the plane defined by said fan beam, said axis substantially intersecting said focal spot;

(c) means for scanning said detector array along a curved path defining an arc having a center substantially coincident with said focal spot, said scanning motion being in a direction substantially perpendicular to the plane defined by said fan beam:

(d) means for scanning said fan beam synchronously with said scanning motion of said detector array, said scanning of said fan and said detector array each being substantially centered about said focal spot, and in a direction substantially perpendicular to said plane;

(e) interpretive circuitry coupled to said detector array for producing digital radiographic images;

(f) a plurality of x-ray attenuating calibration elements, each element comprising a gas tight envelope and being curved and defining an arc about a center point substantially coincident with said focal spot, each of said calibration elements being of uniform thickness to present a path of equal length to x-rays from said source penetrating said calibration element, and;

(g) means for attaching one of said calibration elements aligned with said detector array for scanning movement synchronously with the scanning movement with said detector array.

9. A scan projection radiographic imaging system comprising:

(a) an x-ray source defining a focal spot from which x-radiation primarily emanates upon actuation of the source in a generally planar fan shaped beam;

(b) a generally elongated dual energy x-ray detector array spaced from the source and positioned to receive x-rays emanating from said source, said detector array also being curved about an axis substantially perpendicular to the plane defined by said fan beam, said axis substantially intersecting said focal spot;

(c) means for scanning said detector array along a curved path defining an arc having a center substantially coincident with said focal spot, said scanning motion being in a direction substantially perpendicular to the plane defined by said fan beam;

(d) means generating said fan beam synchronously with said scanning motion of said detector array, said scanning of said fan beam and said detector array each being substantially centered about said focal spot, and in a direction substantially perpendicular to said plane;

(e) interpretive circuitry means coupled to said detector array for producing digital radiographic images;

(f) a plurality of x-ray attenuating basis calibration elements, each element comprising a liquid tight envelope and being curved and defining an arc about a center point substantially coincident with said focal spot, each of said calibration elements being of uniform thickness to present a path of equal length to x-rays from said source penetrating said calibration element, and (g) means for attaching one of said calibration elements aligned with said detector array for scanning movement synchronously with the scanning movement of said detector array.

* * * * *